United States Patent [19]  
Perry et al.

[11] 4,425,320  
[45] Jan. 10, 1984

[54] METHOD AND APPARATUS FOR CARRYING OUT SOLID PHASE IN VITRO DIAGNOSTIC ASSAYS

[75] Inventors: David A. Perry; Peter Stead, both of Portland, Me.

[73] Assignee: Ventrex Laboratories, Inc., Portland, Me.

[21] Appl. No.: 307,540

[22] Filed: Oct. 1, 1981

Related U.S. Application Data

[63] Continuation of Ser. No. 93,105, Nov. 13, 1979, abandoned.

[51] Int. Cl.$^3$ ............... G01N 33/54; G01N 33/58; G01T 1/00; B65D 7/00
[52] U.S. Cl. .................... 424/1.1; 422/61; 422/101; 435/7; 436/518; 436/810
[58] Field of Search .......... 424/1; 422/61, 101; 435/7; 436/518, 810

[56] References Cited

U.S. PATENT DOCUMENTS

| | | | |
|---|---|---|---|
| 3,652,761 | 3/1972 | Weetall | 424/12 |
| 3,826,619 | 7/1974 | Bratu, Jr. et al. | 424/1 |
| 3,879,262 | 4/1975 | Schuurs et al. | 424/12 |
| 3,896,217 | 7/1975 | Johnson | 424/1 |
| 3,932,141 | 1/1976 | Beau et al. | 424/1 |
| 4,012,200 | 3/1977 | De Leeuw | 134/21 |
| 4,015,941 | 5/1977 | Kurata | 422/61 |
| 4,053,284 | 10/1977 | Posch | 424/1 |
| 4,065,358 | 12/1977 | Kawai et al. | 422/61 |
| 4,066,646 | 1/1978 | Le Blanc, Jr. et al. | 23/230 B |
| 4,116,638 | 9/1978 | Kenoff | 422/99 |
| 4,133,639 | 1/1979 | Harte | 424/1 |
| 4,135,884 | 1/1979 | Shen | 424/1 |
| 4,197,287 | 4/1980 | Piasio et al. | 424/1 |
| 4,225,575 | 9/1980 | Piasio et al. | 424/1 |
| 4,305,924 | 12/1981 | Piasio et al. | 424/1 |
| 4,378,344 | 3/1983 | Piasio et al. | 436/500 |

FOREIGN PATENT DOCUMENTS

| | | | |
|---|---|---|---|
| 2343763 | 4/1974 | Fed. Rep. of Germany | 422/61 |
| 2902339 | 7/1979 | Fed. Rep. of Germany | 422/61 |
| 2404466 | 6/1979 | France | 422/101 |

*Primary Examiner*—Christine M. Nucker

[57] ABSTRACT

A fluid receptacle is provided with a retainer on the inner surface thereof for confining at least the reactive portion of a coated insert matrix within the receptacle during inversion thereof. The insert has a configuration permitting fluid to be poured into the receptacle and decanted from the receptacle by inversion of the receptacle with the reactive portion of the insert confined therein. The various decanting, washing and measuring operations involved in an assay may therefore be performed while the insert remains confined within the original receptacle, eliminating the need for additional receptacles and for manual assembly or disassembly operations during the assay.

19 Claims, 5 Drawing Figures

METHOD AND APPARATUS FOR CARRYING OUT SOLID PHASE IN VITRO DIAGNOSTIC ASSAYS

This application is a continuation of application Ser. No. 93,105, filed Nov. 13, 1979, now abandoned.

BACKGROUND OF THE INVENTION

1. Field of the Invention

The present invention relates to an improved method and apparatus for carrying out solid phase in vitro diagnostic assays.

2. Description of the Prior Art

In recent years, numerous techniques have been employed in the area of laboratory diagnostics to simplify operating procedures of existing methods and to provide new methods of improved, speed, sensitivity, and accuracy. In particular, solid phase reactions have been especially valuable in simplifying the manipulations of prior art procedures and making possible procedures that could not be performed with conventional homogeneous phase reactions.

A solid phase reaction is generally carried out between one reactant, the fixed component, immobilized on the surface of an insoluble support matrix, and a second reactant, the mobile component, in solution. The reaction occurs when a molecule or a molecular arrangement of the mobile reactant, in the course of diffusion, collides with a molecule of the fixed reactant immobilized on the surface of the solid support matrix. The reaction may be a conventional chemical reaction, a binding of the mobile component by the fixed component as in an immunochemical reaction between an antigen and an antibody, or it may be a binding of the mobile component by the fixed component accompanied by chemical transformation of one of the components such as occurs in an enzyme-catalyzed reaction. Quantitative results are obtained by measuring the formation of products or disappearance of reactants as in the case of conventional and enzyme-catalyzed reactions, and in measuring the amount of the mobile component bound or the amount of mobile component unbound, in the case of an immunochemical reaction.

Any conventional chemical reaction or enzyme-catalyzed reaction resulting in a directly or indirectly measurable change can, in principle, be carried out by solid phase techniques. Directly measurable changes include changes in pH, light absorbance in the visible and ultraviolet regions or changes in fluorescence intensity. Indirect measurements can be made whenever the primary reactants or products are not readily measurable themselves by interposing the action of a reagent to carry out further reaction steps resulting in a measurable change and by the introduction of specific separation techniques. Such strategies may be employed alone or in combination, as is understood in the art.

Where the reaction consists solely of binding, in the absence of chemical change, techniques developed in the field of immunochemistry may be used to measure the extent of the reaction. Solid phase reactions are especially suited for immunochemical assays because the reactants in bound form may readily be removed from the solution by virtue of their attachment to the solid phase. Frequently, however, the components bound in an immunochemical reaction cannot be directly measured because they are indistinguishable by chemical methods from other substances commonly present in the same reaction mixture, so that the mere disappearance of a reactive component from solution or its accumulation on the solid phase cannot be measured directly. Therefore, additional steps must be taken in order to make a measurable change related to the amount of binding.

The variety of approaches taken by workers in the prior art can be grouped into two general categories. In the first of these, termed competitive or indirect immunoassays, the immobilized component is present in controlled amount and the mobile component present in unknown amount. To the unknown amount of mobile component is added a known amount of the same component which has been tagged by the addition of a measurable substituent which does not interfere with its immunochemical reactive properties. The tag may consist of a radioisotope, a chromophore, a fluorophor or an enzyme. The amount of tagged material bound immuno-chemically to the solid phase will depend upon the amount of untagged component in solution competing for the same binding sites. The more of the unknown present, the less will be the amount of tagged component bound.

In the second general method, termed the sandwich method or direct method, the solid phase containing an amount of immunochemically bound mobile component resulting from the first immunochemical reaction is subjected to the action of a reagent which can also bind immunochemically to the solid phase, but only at sites already occupied by the immunochemically bound mobile component. The reagent may be tagged, for example, as in the first method with a radioisotope, a fluorophor, a chromophore or an enzyme. The amount of tagged reagent bound is a direct meaasure of the amount of mobile component bound, which, in turn, is a measure of the amount of mobile component initially present in the reaction mixture.

Where the tag is a radioisotope, the technique, whether competitive or noncompetitive, is termed a radioimmunoassay. When the tag is an enzyme, the assay is termed an enzyme-linked immunoassay. The amount of enzyme-tagged reactant is measured by any convenient method for measuring the activity of the enzyme used in the tag.

Other kinds of solid phase reactions of the type generally described hereinabove are presented by way of example. The immunoradiometric assay for quantitative determination of an antigen is conducted by first reacting a known excess of labeled antibody with the unknown amount of antigen in a homogeneous phase reaction. Subsequently, immobilized antigen in excess amount is added in order to bind the unreacted soluble labeled antibody. The amount of unknown antigen is determined by measuring the difference between the total labeled antibody and the amount bound to the solid phase. The method gives direct quantitative results only with an univalent antigen, i.e., antigen which can only bind one molecule of antibody.

Immunochemical assays are highly useful in clinical research and diagnosis. They are highly specific, owing to the highly selective nature of antigen-antibody reactions. The antigen-antibody binding is very tight so that once the binding reaction has had an opportunity to occur, the limit of detectability is determined by the measurability with which the tag can be detected. Immunochemical assays are exceedingly versatile, owing to the fact that they can be used to measure specific substances selectively against a background of chemically similar substances. Because of these desirable attributes, there has been considerable interest in improving the ease of manipulation, sensitivity, accuracy, speed and applicability of immunochemical assays. The development of solid phase immunoassays has been one of the major advances in the field.

Among the advantages of solid phase systems is that the reaction product or products can be separated from the reaction solution with relative ease, i.e., by physically removing the solid phase material. This is in contrast with a non-solid phase or a homogeneous reaction, which typically results in a homogeneous solution which requires more complex separation techniques.

The introduction of solid phase technology has permitted the performance of novel procedures that were heretofore extremely difficult using free solution technology. An example of this is the sandwich assay technique described hereinabove. While a sandwich assay is theoretically possible in a homogeneous solution, it is not desirable for practical reasons. The most important aspect which makes such assays impractical is that the separation of the first antigen-antibody complex from a homogeneous phase solution requires the use of sophisticated physical-chemical techniques, especially if the antigen is relatively small compared to the antibody and molecular weight differences between free antibody and complexed antibody are slight. The separation procedure in a solid phase system, by contrast, is a matter of relative simplicity.

In solid phase technology, the reagent or reagents used in the procedure are usually immobilized by being coated or bonded, either covalently or by adsorption to the solid phase material, which is then immersed in the sample to be tested. The manner of coupling such reagents to the solid phase material is known. See, for example, the disclosures in U.S. Pat. No. 3,652,761, U.S. Pat. No. 3,879,262 and U.S. Pat. No. 3,896,217.

Examples of commonly used solid phase materials include, but are not limited to, glass or polymeric tubes which are coated with the reagent or reagents on their internal surfaces, coated polymeric inserts, micro and macro beads formed of polymers and of glass, porous matrices, coated membranes, and tablets.

Particularly useful are the coated polymeric insert matrices described in copending U.S. application Ser. No. 905,552, of Piasio et al., filed May 15, 1978 and assigned to the assignee of the present invention. The coated inserts described herein include a handle member having attached at one end a plurality of elements having essentially smooth plane or curved surfaces with the fixed component immobilized thereon. These inserts, which in the preferred embodiment take the form of a central rod having a number of fins extending outwardly from the rod along a portion of its length, are characterized by a large ratio of solid phase surface area to fluid sample volume and by a short average diffusion distance between the molecules of mobile component in the fluid sample and the fixed component distributed on the solid phase surface. These factors contribute to an enhancement of the reaction rate and a consequent reduction in the time required to carry out a given diagnostic assay.

Moreover, since the inserts described in copending application Ser. No. 905,552 extend substantially throughout the depth of the fluid sample and preferably above the surface of the fluid sample as well, an essentially constant geometric relationship exists between the fluid volume and the solid phase surfaces of the insert matrix throughout the depth of the fluid sample, such relationship being preserved despite changes in the fluid volume. This factor tends to produce more uniform results and to minimize the effect of human error when a number of assays are performed sequentially or concurrently.

As disclosed in copending U.S. application Ser. No. 064,389, of Piasio et al., filed Aug. 8, 1979 and also assigned to the assignee of the present invention, the reaction kinetics may be further enhanced by coating the inner surface of the fluid receptacle with the same fixed component that is applied to the surfaces of the solid phase insert matrix. This has the effect of further increasing the ratio of the solid phase surface area to fluid sample volume and hence the effective concentration of the fixed component, and further reducing the average diffusion distance between the mobile and fixed components. In this way reaction equilibrium is reached more quickly, and the reliability of the assay improved, as compared with assays conducted using coated inserts or coated receptacles alone.

Despite the high level of refinement exhibited by present-day solid phase immunoassay techniques, certain difficulties still exist when immunoassays are performed on a large scale, as it typically the case in hospitals and clinical testing laboratories. These difficulties arise not from any inherent limitations in the basic solid phase reaction technology, but rather from the redundant and time-consuming physical manipulations that are required for carrying out multiple simultaneous or sequential immunoassays using presently available equipment.

The nature of the above-mentioned manipulative difficulties may be readily apprehended by first considering a competitive or indirect radioimmunoassay carried out using a coated polymeric insert and a fluid receptacle (e.g., a test tube) for receiving the insert and the fluid sample to be assayed. The insert may take the form of a central rod or stick having a number of fins extending outwardly from the rod along a portion thereof, as described in the aforementioned copending application Ser. No. 905,552. The fins may, but need not, be made to conform approximately to the shape of the test tube or other receptacle in which the insert will be received. The portion of the central rod not having fins attached thereon serves as a handle member, facilitating the introduction of the fin-bearing portion of the insert into the fluid receptacle and avoiding the necessity of touching and possibly contaminating the antibody immobilized on the fin surfaces.

Typically, the fluid sample containing both the unknown and radioactively tagged mobile components is introduced into the test tube prior to the insertion of the finned insert matrix into the tube. The subsequent introduction of the insert matrix into the test tube then marks the start of the reaction for timing purposes. Alternatively, the fluid sample may be introduced into the test tube with the insert matrix already in place therein, which will be the procedure followed when, for example, the fixed component is immobilized on the inside surface of the test tube as well as on the reactive surfaces of the insert matrix, as taught in the aforementioned copending application Ser. No. 064,389. The finned stick is a particularly suitable insert when this alternative procedure is elected, since the open interstices between adjacent fins permit substantially unimpeded pouring of the fluid sample into the receptacle while the insert is in place therein.

After a suitable reaction interval has elapsed, the reaction is stopped by separating the insert matrix from the fluid sample so that no further binding of the mobile components to the fixed component can take place. This is usually done by removing the insert matrix from the reaction tube and washing it in a further test tube containing water or a wash buffer. The washing operation removes most of the tagged and untagged mobile components that are not actually immunochemically bound to the antibody immobilized on the fin surfaces of the insert matrix. After washing, the insert matrix is removed from the wash fluid and placed in a further clean test tube for measurement in a suitable radioactive counting chamber. A scintillation fluid is often introduced into the test tube used in this measurement in order to enhance the radioactive count obtained.

It is apparent that the procedure outlined above requires at least three test tubes and two insert matrix removal and reinsertion operations in order to carry out a single complete assay. It is possible to reduce the number of test tubes required to two by rinsing either the reaction tube or the wash tube and re-using it for the measuring operation, but this increases the number of manipulative operations that the technician must perform and hence the time required for the assay as a whole. The use of fewer than two tubes would not be in accord with proper laboratory procedure, since a second test tube is required for safely confining the now-radioactive insert while the first is decanted and rinsed for re-use in the measuring operation. The insert might easily slip out of its test tube if decanting and rinsing were to be attempted while it was in place, possibly contaminating the laboratory environment or the reactive surfaces of the insert as a result.

In the case of the sandwich or direct radioimmunoassay method, it will be recalled that two distinct immunochemical reactions must be carried out. The first is the binding of the unknown mobile component to be fixed component immobilized on the solid phase insert surfaces, and the second is the binding of the tagged reagent to the sites on the solid phase matrix already occupied by the unknown mobile component that was bound during the first reaction. Since these two reactions are usually carried out sequentially, using separate reaction fluids for the respective unknown and tagged mobile components, it is apparent that the direct radioimmunoassay will ordinarily require one more test tube than the indirect radioimmunoassay described previously. While it is possible to carry out the two reactions essentially simultaneously in the same tube, it is clear that the number of test tubes and manipulative operations required to perform the assay will still be at least as great as in the case of the indirect or competitive method.

Viewed in the context of a single assay, the number of test tubes and manipulative operations required may not appear to be a major consideration. In hospitals and testing laboratories where assays are regularly performed in large numbers, however, these factors take on considerable importance. The number of clean test tubes that must be kept on hand to carry out a particular assay method, and the time required for performing the various manual operations attending its use, may well be determinative of the commercial feasibility of adopting the assay method for large scale use.

From the standpoint of laboratory procedure, prior art coated tube assays possessed the undeniable advantage of simplicity, requiring no assembly or disassembly steps and usually no additional test tubes for performing the assay. The improved reaction kinetics made possible by the advent of the coated insert matrix, however, render these assays more desirable than coated tube methods despite the added procedural complexity involved in handling the insert as a separate and removable part of the assay assembly. Ideally, it would be desirable to combine the procedural advantages stemming from unitary structure, as exhibited by the coated tube assay systems, with the flexibility and reaction efficiency that characterize coated insert systems.

This ideal has been realized only imperfectly in the prior art. U.S. Pat. No. 4,116,638, for example, describes a solid phase support structure consisting of a number of capillary tubes retained by a circular disk which forms an airtight seal against the interior of a reaction vessel. A central tube of greater diameter than the capillary tubes is said to be usable for the introduction of reactive and wash solutions into the vessel or for their removal from the vessel by suction, but the introduction of a fluid into the vessel by a simple manual pouring operation would appear to be impractical given the narrow diameter of the central tube relative to the diameter of the mouth of the vessel. Moreover, it would appear that the circular disk would prevent complete decanting of the fluid in the vessel if the whole apparatus were simply inverted. In order to insure complete draining of the vessel, therefore, the technician performing the assay must either attach an external source of suction to the central tube, or remove the support structure as a whole from the reaction vessel.

U.S. Pat. No. 4,066,646 describes a combined diagnostic device and tubular housing assembly which includes a cap for sealing the open end of the tubular housing. The cap also serves as the support for a depending rod which extends downwardly toward the fluid sample contained in the tubular housing. The lower end of the rod in turn supports a thin sheet of substrate material having a biologically active layer thereon for immersion in the fluid sample. Although an essentially unitary structure is thereby provided, it is apparent that the cap prevents pouring of a fluid sample into the tubular housing, as well as decanting of the fluid sample and rinsing of the substrate, while the apparatus remains assembled.

SUMMARY OF THE INVENTION

In accordance with the present invention, coated insert assay procedures are simplified by providing the fluid receptacle in which the insert is received with a retainer on the inner surface thereof for effectively confining at least the reactive portion of the insert within the fluid receptacle when the receptacle is inverted. The insert has a configuration which permits fluid to be poured into the fluid receptacle and decanted from the fluid receptacle during inversion of the receptacle with the reactive portion of the insert confined therein. The various decanting, washing and measuring operations involved in a radioimmunoassay, for example, may therefore be performed while the insert remains safely confined within the original reaction test tube. In this way, the number of test tubes required for carrying out a complete radioimmunoassay is reduced to one. Moreover, the need for manual assembly or disassembly operations subsequent to the initial introduction of the insert into the reaction tube is eliminated entirely, with a concomitant improvement in safety.

In the preferred embodiment of the invention, the solid phase insert matrix comprises a handle member in the form of a rod having a number of outwardly-projecting fins attached near one end thereof. The fixed component, usually an antibody in the case of an immunoassay, is immobilized on the surfaces of the fins, which therefore constitute the reactive portion of the insert. The fluid receptacle is preferably a test tube, and the retainer on the inner surface of the tube is a convex projection which may be conveniently created by forming a concave indentation on the outside surface of the tube.

The dimensions of the convex projection are sufficient to normally obstruct the insertion of the fin-bearing portion of the insert matrix into the test tube or its removal therefrom once inserted, but there is sufficient resiliency either in the insert matrix or in the test tube, and preferably in both, to permit the fin-bearing portion of the insert to be pushed past the projection for initial insertion into the test tube. Thereafter, the projection acts to confine the fin-bearing portion of the insert matrix within the test tube even when the tube is completely inverted. Since the open interstices between adjacent fins of the insert matrix will allow fluids to be freely poured into or decanted from the test tube when the insert matrix is in place, the assembled tube/insert combination may be decanted, washed, refilled or otherwise handled during the assay procedure essentially as if it were of one-piece construction.

The convex projection is preferably spaced from the mouth of the test tube by a vertical distance sufficient to allow the fin-bearing portion of the insert matrix to remain stably poised adjacent the mouth of the test tube, supported by the projection and by the vertical side walls of the tube, prior to being pushed past the projection and thereby fully inserted into the tube. This not only provides a convenient resting place for the insert just prior to starting the reaction, but also enables the reaction to be started at a well-defined point in time by means of a simple, abrupt downward push on the handle portion of the insert.

The convex projection is preferably also spaced from the bottom of the test tube by a distance substantially greater than the length of the fin-bearing portion of the insert matrix, so that the insert matrix will tend to separate from the bottom of the tube when the tube is in an inverted condition, as during decanting. This assists in displacing fluid which may tend to become lodged in the area between the bottom of the tube and the bottom of the fin-bearing portion of the insert matrix, and thereby enhances the drainage of fluid from the test tube.

BRIEF DESCRIPTION OF THE DRAWINGS

The various objects, advantages and novel features of the invention will be more readily apprehended from the following detailed description when read in connection with the accompanying drawing figures, in which.

DETAILED DESCRIPTION OF THE PREFERRED EMBODIMENT

Figure 1:
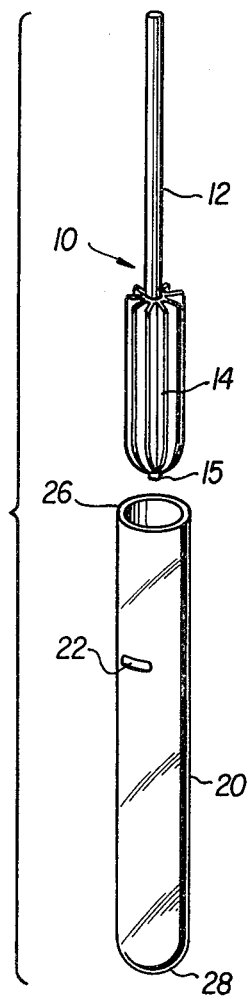
FIG. 1 illustrates a finned insert matrix and an indentation-bearing test tube in accordance with the preferred embodiment of the invention.

FIG. 1 illustrates a finned insert matrix 10 and corresponding fluid receptacle 20 in accordance with the preferred embodiment of the present invention. Insert matrix 10 comprises a central rod 12 and a plurality of equally spaced, radially projecting fins 14 attached to the central rod 12 along the lower portion thereof. The upper portion of the rod 12 to which fins are not attached serves as a handle to facilitate insertion of the insert matrix 10 into the receptacle 20. The fins 14 are preferably formed as part of a unitary structure which includes the central rod 12; alternatively, the fins may be attached to the rod by means of physical connections such as a tongue and groove, or by means of a suitable adhesive. A small button 15 is provided on the bottom of the insert below the fins 14 for a purpose to be described hereinafter.

The insert matrix 10 may be fabricated from virtually any water-insoluble material, such as polymethacrylate, polypropylene or polystyrene, and is preferably of the type described in the aforementioned copending application Ser. No. 905,552, which application is expressly incorporated herein by reference. The fins 14 have the fixed component of the solid phase reaction immobilized thereon, which will ordinarily be an antibody in the case of an immunological binding reaction, and therefore constitute what may be referred to as the reactive portion of the insert matrix. Preferably, the insert matrix includes nine equally spaced fins 14 attached to the central rod 12, although a greater or lesser number of fins could be employed. As disclosed in the aforementioned copending application Ser. No. 905,552, inserts having twelve, sixteen and eighteen fins have all been found to exhibit favorable reaction kinetics. The fins 14 may be shaped to conform approximately to the inside of the receptacle 20 in the manner shown for a smooth mechanical fit, but this is not essential from the standpoint of the solid phase reaction kinetics.

Figure 2:
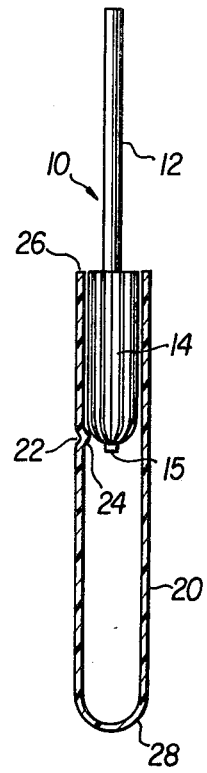
FIG. 2 depicts a cross-section of the test tube of FIG. 1, showing the insert poised adjacent the mouth of the tube prior to being fully inserted therein.

Fluid receptacle 20 is preferably a standard 12×75 millimeter polystyrene test tube which may have a rounded bottom 28 as shown, or a flat bottom if desired. The cross-section of the tube 20 may be circular, as shown, or may assume any other desired configuration. In accordance with the present invention, however, the tube 20 has been modified by forming an elongated concave indentation 22 on the outer vertical wall surface thereof. As a result of the indentation 22, a corresponding elongated convex projection 24 (visible in the cross-sectional views of FIGS. 2–4) occurs on the inner vertical wall surface of the tube 20. The preferred method of forming the indentation 22, and thus the projection 24, will be described in some detail hereinafter. For present purposes, it is important only to point out that the inwardly-projecting dimension of the projection 124 restricts the diameter of the tube 20 by an amount sufficient to normally (i.e., without the application of external force) prevent the full insertion of the fin-bearing portion of the insert 10 into the tube, as depicted in FIG. 2, and to normally confine the fin-bearing portion of the insert 10 within the tube 20 once it has been inserted therein even when the tube is fully inverted, as depicted in FIG. 4. Either the insert 10 or the tube 20, however, and preferably both, possesses sufficient resiliency to permit the fin-bearing portion of the insert 10 to be manually pushed past the projection 24 and thereby fully inserted into the tube 20, as shown in FIG. 3.

When the insert 10 is polymethacrylate, for example, and the tube is polystyrene, as in the preferred embodiment, sufficient mutual resiliency is present to allow the insert 10 to be pushed past a properly dimensioned projection 24 with only moderate manually-applied force. It is apparent that a glass test tube could also be used, as long as the insert 10 has some resiliency and the projection 24 is of suitable dimensions. Conversely, an unyielding insert could be used, assuming some resiliency in the test tube 20 and a properly dimensioned projection 24.

Figure 3:
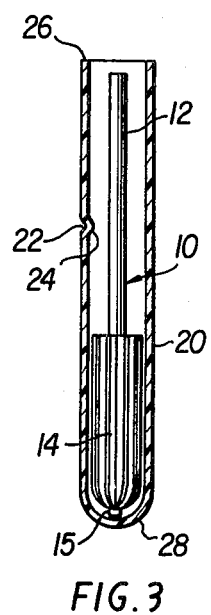
FIG. 3 depicts a further cross-section of the test tube of FIG. 1, showing the insert matrix fully inserted therein.
Figure 4:
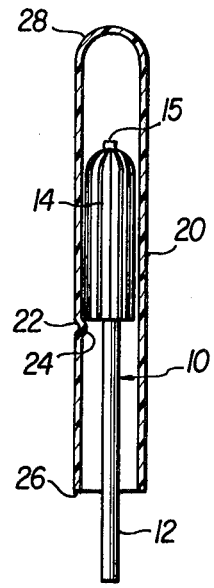
FIG. 4 depicts a further cross-section of the test tube of FIG. 1, showing the tube in an inverted condition for draining a fluid therefrom.

With the insert 10 in place within the tube 20 as shown in FIG. 3, it is apparent that the tube/insert combination can be decanted, washed, refilled and otherwise handled during the course of an assay as if it were of unitary construction, the projection 24 serving to confine the reactive or fin-bearing portion of the insert within the tube even during full inversion of the tube, as depicted in FIG. 4. By virtue of the open interstices between adjacent fins 14, fluid can be introduced into or decanted from the tube 20 in a substantially unimpeded manner while the insert matrix 10 is in place therein. Clearly, any impermeable unitary insert, finned or otherwise, which has a configuration permitting fluid to be poured into and drained from the tube 20 while in place therein could be substituted, but the nine-fin insert shown is preferred because it combines good fluid drainage with particularly favorable solid phase reaction kinetics.

Assuming that a fin-bearing insert 10 of the type described is in fact used, the elongated projection 24 should extend sufficiently far around the inner circumference of the tube 20 to bridge at least two adjacent fins 14. This renders it impossible for the fins 14 to become aligned in a manner permitting them to slip past the projection 24 unimpeded, and therefore insures that the insert 10 and tube 20 will not become unintenionally separated during the decanting and washing operations.

As shown in FIG. 2, the projection 24 is preferably spaced from the mouth 26 of the test tube 20 by a distance sufficient to allow the fin-bearing portion of the insert 10 to remain stably poised adjacent the mouth of the tube, supported by the vertical side walls of the tube and by the projection 24, prior to being pushed past the projection and into the tube to assume the fully inserted portion illustrated in FIG. 3. This is advantageous for at least two reasons. First, it provides a convenient resting place for the insert prior to the start of the assay. This reduces the chance that the coated fin surfaces will become contaminated by foreign matter as a result of being placed, for example, on the laboratory bench prior to commencing the assay. In addition, the ability of the insert to remain stably poised adjacent the mouth of the tube 20 as shown in FIG. 2 enables the assay to be started at a well-defined point in time by means of a simple, abrupt downward push on the handle portion 12 of the insert 10, whereby the fixed component on the coated surfaces of the fins 14 becomes promptly immersed in the mobile component contained in the fluid sample in the lower portion of the tube 20. The required downward push may even be applied to many poised inserts simultaneously by means of a rigid mechanical arm or the like, whereby the assay assembly of the present invention may be readily adapted to full or partial automation on a large-scale basis.

FIG. 2 shows the spacing between the projection 24 and the mouth 26 of the test tube 20 to be approximately equal to the length of the fin-bearing portion of the insert matrix 10, so that the entire fin-bearing portion is enclosed within the side walls of the tube 20 when the insert is poised for insertion. This is the minimum preferred spacing between the projection 24 and the mouth 26, since it insures that the entire reactive portion of the insert 10 will be enclosed by the vertical side walls of the tube 20 and thereby shielded from possible contamination during the time that the insert is poised adjacent the mouth of the tube prior to the start of the assay. It is apparent, however, that a smaller spacing between the projection 24 and the mouth 26 of the tube 20 will suffice to permit the insert to remain stably poised at the mouth of the tube if the shielding function is not required.

According to a further aspect of the preferred embodiment of the present invention, the projection 24 is spaced from the bottom 28 of the tube 20 by a distance substantially greater than the length of the fin-bearing portion of the insert matrix 10, as will be readily apprehended from FIG. 3. As a result, inversion of the tube 20 causes the fin-bearing portion of the insert to drop toward and abut the projection 24, as depicted in FIG. 4. This permits the bottom of the fin-bearing portion of the insert 10 to separate from the bottom 28 of the tube 20, thereby displacing the fluid which tends to become lodged in that area and hence encouraging the complete drainage of fluid from the tube 20. The sudden jarring of the fin-bearing portion of the insert 10 against the projection 24 during inversion of the tube 20 also tends to shake loose any fluid adhering to the surfaces of the fins 14, further promoting complete drainage. This effect may be enhanced by repeated manual shaking of the tube 20 during decanting, which will cause the fin-bearing portion of the insert 10 to repeatedly strike the projection 24.

Preferably, a small button 15 is formed on the bottom of the fin-bearing portion of the insert 10 to prevent close contact between bottom edges of the fins 14 and the bottom of the tube 20 when the insert assumes the fully inserted position shown in FIG. 3. An advantage of the button is that it reduces fluid surface tension effects which might otherwise hamper the separation of the insert from the bottom 28 of the tube during inversion of the tube. This button is not deemed essential for this purpose, however, because the weight of the insert 10 will in most instances be sufficient to insure its separation from the bottom of the inverted tube regardless of any such fluid surface tension effects.

In an exemplary embodiment, using a standard $12 \times 75$ millimeter polystyrene test tube 20 as previously noted, the fin-bearing portion of insert 10 may be approximately 28 millimeters in length and the projection 24 would therefore be spaced by approximately 28 millimeters from the mouth 26 of the tube 20 in order to enclose the fin-bearing portion of the insert completely within the vertical side walls of the tube when the insert is in its poised position. In practice, the projection 24 may be spaced somewhat closer to the mouth 26 of the tube 20 if the bottoms of the fins 14 are rounded as shown, since the rounded bottoms of the fins 14 will tend to extend slightly past the projection 24 when the insert is in its poised position, as will be apparent from an inspection of FIG. 2. In any event, roughly 45–50 millimeters will remain between the bottom of the tube and the projection, which allows more than adequate separation between the fin-bearing portion of the insert and the bottom of the tube during inversion thereof to accomplish the drainage enhancement function described previously. Adequate spacing for both drainage enhancement and for poising and shielding the insert at the mouth of the tube will be provided, in fact, if the projection is instead simply located at or near the center of the tube.

As shown in FIG. 3, the upper extremity of the handle portion 12 of the insert 10 terminates a few millimeters below the mouth 26 of the test tube 20 when the insert 10 is fully inserted therein. This insures that no protruding handle will cause splashing or otherwise interfere with the pouring of fluids into the tube once the insert has been fully inserted, as for example when a second reaction fluid is introduced into the assembled tube/insert combination during the course of a sandwich or direct assay. In practice, therefore, the handle portion 12 should be no longer than is required for inserting the fin-bearing portion of the insert 10 past the convex projection 24 and into the tube 20. Clearly, this length will be dictated by the distance by which the projection 24 is spaced from the mouth 26 of the tube.

The usefulness of the present invention in connection with solid phase immunoassays, and particularly radioimmunoassays, will now be apparent. Assuming that a fluid sample containing the unknown mobile component and radioactively tagged mobile component has been placed in the tube 20, as will be the case in a competitive or indirect radioimmunoassay, coated insert 10 is then placed into the mouth 26 thereof so that it assumes the poised position shown in FIG. 2. The solid phase reaction is then started by means of an abrupt downward push on the handle portion 12 of the insert, whereby the fin-bearing portion of the insert is forced past the projection 24 and immersed in the fluid sample at the bottom of the tube 20. The downward push may be applied manually or, as noted previously, by a rigid mechanical arm or the like, the latter alternative being especially useful when it is desired to start several assays simultaneously. In either case, the relationship of the insert 10 and the tube 20 after the solid phase reaction has been initiated is illustrated in FIG. 3.

It is possible, of course, to push the insert 10 fully into the tube 20 prior to introducing the fluid sample. In that case, the start of the solid phase reaction is marked by the subsequent pouring of the fluid sample into the tube. This procedure will be followed when, for example, the fixed component of the solid phase reaction is coated on the inside surface of the tube 20 as well as on the surfaces of the fins 14. The advantages of this combination are taught in the aforementioned copending application Ser. No. 064,389, which application is expressly incorporated herein by reference.

When the desired reaction time has expired, the reaction is stopped by inverting the tube/insert combination as shown in FIG. 4 and decanting the fluid sample. This, too, may be done mechanically rather than manually, as for example by means of an invertable test tube rack which may accommodate a number of tubes 20. In either case, the fin-bearing portion of the insert 10 separates from the bottom 28 of the test tube 20 during inversion thereof and drops against the projection 24 in order to promote the drainage of fluid from the bottom of the tube as explained previously. When the tube is being handled manually, it may be repeatedly shaken to cause the insert to repeatedly strike the projection 24 in order to shake loose the fluid adhering to the surfaces of the fins 14, thereby further promoting complete fluid drainage. During the decanting operation, projection 24 acts to confine the reactive or fin-bearing portion of the insert 10 within the tube 20, although the handle portion 12 may protrude somewhat as shown in FIG. 4.

After the fluid sample has been decanted, water or a wash buffer may be poured into the tube 20 in order to remove from the surfaces of fins 14 most of the tagged and untagged mobile components that are not actually immunochemically bound thereto. After suitable agitation, the wash fluid may be decanted by inversion of the tube 20 as described previously, the projection 24 again serving to confine the insert 10 therein. The tube/insert combination may now be placed as a whole into a radioactive counting chamber for the measurement operation, perhaps after introducing a scintillation fluid into the tube in order to enhance the radioactive count obtained.

Considering now the case of a sandwich or direct radioimmunoassay, it will be recalled that two immunochemical reactions are carried out rather than one. The first is the binding of the unknown mobile component to the fixed component immobilized on the reactive portion of the insert 10, and the second is the binding of the radioactively tagged reagent to the sites on the insert surfaces already occupied by the unknown mobile component that was bound during the first reaction. These reactions are usually carried out sequentially using separate reaction fluids for the respective unknown and tagged mobile components. Accordingly, in the case of a sandwich or direct radioimmunoassay, the above-described procedure is modified slightly, since it is necessary to introduce and decant two reaction fluids rather than one. These operations are all carried out, however, while the insert 10 remains confined within the same test tube 20.

Regardless of whether the radioimmunoassay is direct or indirect, it will be apparent that the present invention allows the assembled insert 10 and tube 20 combination to be handled essentially as if it were of one-piece construction once the assay has been commenced. No assembly or disassembly steps are required subsequent to the original insertion of the insert into the tube, thus minimizing the manipulative complexity of the assay for the technician. Moreover, the entire assay procedure is carried out using only one test tube, thereby rendering the assay economically attractive, particularly for large scale use.

Although the present invention is broadly applicable to any type of solid phase assay, it is particularly suited for use in radioimmunoassays, where a radioactive tag binds to the reactive portion of the insert 10. By allowing the reactive portion of the insert to remain safely confined within the test tube 20, the invention dispenses with the need to provide separate confinement for the radioactive insert while the tube is emptied of the reaction fluid and rinsed. Moreover, since the radioactive counting operation can usually be performed while the insert 10 remains confined within the tube 20, the radioimmunoassay can be performed from start to finish without removing the insert from the original reaction tube.

The invention is also of particular utility when, as described in the aforementioned copending application Ser. No. 064,389, the fixed component of the solid phase reaction is immobilized on the inside surface of the tube 20 as well as on the insert matrix 10. In this case the tube and the insert each form a part of an overall solid phase matrix surface. It is clearly desirable to prevent them from becoming unintentionally separated, and possibly irretrievably intermingled with other tubes and inserts, prior to the completion of the measuring operation. The instant invention renders the possibility of such unintentional separation highly unlikely.

It will be readily apprehended that the present invention is equally applicable to both quantitative and qualitative assays. In the latter case, the purpose of the aforementioned measuring operation is simply to determine the presence of a minimum threshold amount of mobile component, rather than to determine the absolute amount of mobile component.

It will also be appreciated that, while the present invention is of particular utility in connection with radioimmunoassays, it is not limited thereto. Both colorimetric and enzyme-linked assays, for example, may also be performed using the method and apparatus of the present invention.

Figure 5:
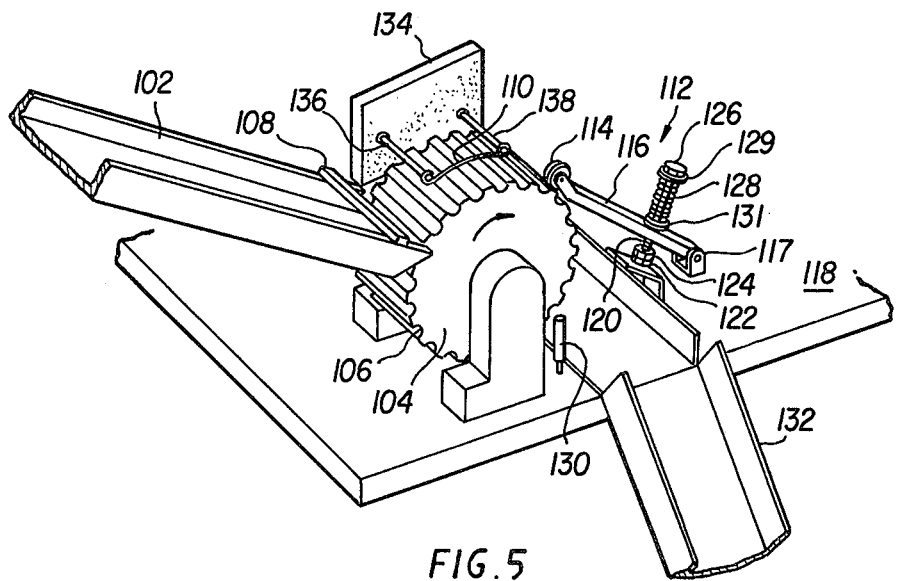
FIG. 5 illustrates an automatic apparatus for providing polymeric test tubes with suitable indentations.

FIG. 5 is a perspective view of an automatic apparatus for forming suitable elongated indentations on the outer wall surfaces of polymeric test tubes. Blank polystyrene 12×75 millimeter tubes (not shown) are fed individually from a supply tray 102 to a rotating wheel 104 which is provided with slots 106 for receiving the individual tubes. Guide bar 108 insures that only one tube at a time is loaded onto the slotted wheel 104.

As the slotted wheel 104 rotates in the direction indicated by the arrow, the tubes carried in the slots 106 are exposed to the localized radiant heat provided by heating element 110. Element 110 is spaced by a small distance from the slotted wheel 104 and has an arcuate configuration so as to follow the circumference thereof. The purpose of heating element 110 is to heat-soften the precise area of the tubes where indentations will subsequently be formed by the spring-biased follower device 112.

Follower device 112 includes a sharp-edged roller 114 which is rotatably mounted at one end of a pivoted spring-biased arm 116. Roller 114 is arranged to make rolling contact with the heat-softened area of each polymeric tube shortly after the tube passes out of the heating zone defined by arcuate heating element 110. The sharpened edge of the roller 114 then serves to form an elongated indentation at the desired point on each tube.

As may be seen in FIG. 5, a gap is provided between the terminal end 138 of the arcuate heating element 110 and the point of tangency of the roller 114 with the tube-carrying wheel 104. This provides a momentary cooling interval for the tubes as they emerge from the heating zone before they are indented by the roller 114. The purpose of this brief cooling interval is to allow sufficient surface recrystallization of the tubes to avoid sticking of the softened polymeric tube material to the roller 114.

The arm 116 on which roller 114 is rotatably mounted is pivoted at point 117 with respect to base plate 118 in order that roller 114 may follow the uneven contour of the tube-carrying wheel 104. Threaded rod 120, which is fastened at one end to base plate 118, passes loosely through an aperture in arm 116 in order to provide adjustments therefor. Adjusting nuts 122 and 124 are threaded onto rod 120 for abutting the underside of arm 16 in order to adjust the closest approach of the roller 114 to the wheel 104, and hence the depth of the indentations that will be formed in the polymeric test tubes. In a test tube with a circular cross-section, the depth of the indentation will determine its elongation, which should, as noted previously, be sufficient to bridge at least two adjacent fins of the insert matrix with which the tube will be used. Adjusting nut 126 is threaded onto rod 120 above the pivoted arm 116 and serves to adjust the compression on spring 128, thereby setting the indentation pressure applied by the roller 114 to the heat-softened test tubes. Washers 129 and 131 are provided to confine the spring 128 between the adjusting nut 126 and the pivoted arm 116.

After the tubes rotate past the roller 114 and receive an indentation therefrom, they are urged out of the slots 106 in wheel 104 by a suitably positioned peg 130. The finished tubes then drop into collection tray 132 for routing to any subsequent processing or finishing steps.

In the applicants' prototype, roller 114 was made using an ordinary one-quarter inch (normal inside diameter) hardware washer which was sharpened along its circumference so that its edge acquired a triangular cross-section with a slightly rounded apex. The slight rounding of the sharpened edge prevents the roller from cutting through the test tubes during the indentation process, although sufficient sharpness must be preserved to insure that the roller indents, rather than merely collapses, the walls of the heat-softened tubes.

Slotted wheel 104 is, in the prototype, approximately 6.5 inches in diameter with slots 106 dimensioned to accommodate standard 12×75 millimeter polystyrene test tubes. The slotted wheel consists of a phenolic laminate or any other suitably heat resistant material and is arranged for rotation at approximately 3 r.p.m. by means of a suitable constant-speed A.C. motor, gear reducer, and belt drive system, which have been omitted from the drawings for simplicity.

Heating element 110 is a 5 inch strip of nichrome wire which is bent to form an arc subtending approximately 70 degrees relative to the full circumference of the slotted wheel 104. An insulating back plate 134 provides a mounting surface for the electrical terminals 136 and 138 that supply the element 110. Terminals 136 and 138 are supplied by a variable transformer or "Variac", not shown, which allows the amount of heat provided to the tubes on the wheel 104 to be varied. In the prototype a workable power level for heating element 110 has been found to be approximately 135 watts. A spacing of approximately one-sixteenth inch between the heating element 110 and the top surfaces of the test tubes carried by the wheel 104 has been found to be appropriate at this level of heat intensity. A sufficient cooling interval for the test tubes between the heating and indentation operations results when a gap subtending approximately 10 degrees of arc is provided between terminal 138 of the heating element and the tangency point of the roller 114.

Although the present invention has been described with reference to a preferred embodiment, it will be apparent to those skilled in the art that many modifications may be made thereto without departing from the spirit and scope of the invention. The solid phase insert matrix, for example, need not be of the finned type described, but may be any unitary impermeable structure which has a configuration permitting fluid to be poured into and decanted from a fluid receptacle by inversion thereof with the insert matrix confined therein. It may or may not include a handle portion and may or may not conform to the contours of the fluid receptacle. The fluid receptacle need not be a test tube with a rounded bottom as described, but may instead have a flat bottom or a non-circular cross-section, or any other desired configuration. The retainer used for confining the reactive portion of the insert within the receptacle need not be a small convex projection as shown, but may instead be an annular restriction extending completely around the inner circumference of the receptacle, and may be relocated to the mouth of the receptacle to form an annular, inwardly-projecting lip. Alternatively, the retainer may comprise two or more convex projections of the type described herein, located at randomly or evenly spaced positions around the circumference of the receptacle. The retainer may, if desired, be of an asymmetrical configuration so as to permit insertion but not removal of the insert matrix, since removal of the insert matrix from the fluid receptacle is generally not necessary given that measuring operations (e.g., radioactive counting) can ordinarily be performed while the insert remains within the receptacle. The retainer need not even be convex as viewed from the interior of the receptacle, but may instead be an interior recess or indentation for engaging a corresponding projection on the insert as the insert is pushed into the receptacle. Nor is there any requirement that the retainer be structurally continuous with the walls of the receptacle, as in the case of a convex in concave formation therein; the retainer may equally well be a separately-affixed structure. All such alterations and modifications are intended to fall within the scope of the appended claims.

What is claimed is:

1. In a process for carrying out a measurable reaction between a mobile component contained in a fluid sample and a fixed component immobilized on a portion of an impermeable unitary insert matrix, said insert matrix comprising a reactive portion on which said fixed component is immobilized and a handle portion for enabling manual insertion of said insert matrix into a fluid receptacle, and said fluid sample being contained in a fluid receptacle suitable for receiving at least the reactive portion of said insert matrix by manual insertion thereof, the improvement which comprises utilizing, in combination, a fluid receptacle which has a retainer on the inner surface thereof for confining at least the reactive portion of the insert matrix within the fluid receptacle during inversion thereof, said retainer comprising an integral convex projection on the inner surface of the side wall of the receptacle corresponding to a concave indentation formed on the outer surface of the receptacle, and an insert matrix which has a reactive portion characterized by a generally open configuration permitting fluid to be poured into the fluid receptacle through said reactive portion and decanted from the fluid receptacle through said reactive portion by inversion of the fluid receptacle with the reactive portion of the insert matrix confined therein by said retainer, whereby decanting, washing and measuring operations may be performed while the reactive portion of the insert matrix remains confined within the fluid receptacle.

2. The process of claim 1 wherein the fixed component is an antibody, the mobile component is an antigen, and the reaction is the binding of the antigen to the antibody.

3. The process of claim 2 wherein at least a portion of said antigen contains a radioactive label.

4. In a process for determining the amount of mobile component contained in a fluid sample which reacts with a fixed component immobilized on a solid phase insert matrix to produce a measurable change which is a function of the amount of mobile component, comprising the steps of:
 (a) providing a fluid receptacle suitable for receiving at least the reactive portion of an impermeable unitary insert matrix by manual insertion thereof;
 (b) placing in said fluid receptacle
  (i) a fluid sample having an unknown amount of the mobile component which is to be measured, and
  (ii) an impermeable unitary insert matrix having a handle portion for enabling manual insertion of the insert matrix into said fluid receptacle and a reactive portion which is in contact with the fluid sample when inserted therein, said reactive portion having the fixed component immobilized thereon for reacting with the mobile component at a rate or to an extent measurable as a function of the concentration of said mobile component,
 (c) allowing the contents of the fluid receptacle to stand for a given time interval to permit a reaction to occur,
 (d) decanting the fluid sample and washing the insert matrix, and
 (e) measuring the change which is a function of the concentration of the mobile component to determine the amount of the mobile component,
 the improvement which comprises utilizing, in combination, a fluid receptacle which has a retainer on the inner surface of the side wall thereof for confining at least the reactive portion of the insert matrix within the fluid receptacle during inversion thereof, said retainer comprising an integral convex projection on the inner surface of the side wall of said receptacle corresponding to a concave indentation formed on the outer surface of the receptacle, and an insert matrix which has a reactive portion characterized by a generally open configuration permitting fluid to be poured into the fluid receptacle through said reactive portion and decanted from the fluid receptacle through said reactive portion by inversion of the fluid receptacle with the reactive portion of the insert matrix confined therein by said retainer, whereby the decanting, washing and measuring operations may be performed while the reactive portion of the insert matrix remains confined within the fluid receptacle.

5. The process of claim 4 wherein the insert matrix includes a central rod, one end of said central rod forming the handle portion of the insert matrix, and wherein the reactive portion of said insert matrix comprises a plurality of elements attached at the other end of said central rod and having essentially smooth plane or curved reactive surfaces with the fixed component immobilized thereon, said elements being so arranged with respect to one another and the central rod and of a size and shape such that when the insert matrix is inserted into the fluid receptacle, the reactive portion of the insert matrix extends substantially throughout the depth of the fluid sample and the average diffusion distance of molecules of the mobile component to the reactive surfaces of said elements is greatly reduced relative to the average diffusion distance of molecules of said mobile component to the fluid receptacle when no insert matrix is present therein.

6. The process of claim 5 wherein said elements comprise a plurality of fins extending outwardly from said central rod along a portion of the length thereof, and wherein said fluid receptacle includes substantially straight vertical side walls terminating in an open mouth at one end of said receptacle and a closed bottom at the opposite end of said receptacle.

7. The process of claim 6 wherein said retainer comprises a convex projection on the inner vertical side wall surface of said receptacle corresponding to a concave indentation formed on the outer vertical side wall surface of said receptacle, said projection having dimensions sufficient to normally obstruct the insertion of the fin-bearing portion of the insert matrix into the fluid receptacle and its removal therefrom, and wherein at least one of said insert matrix and said fluid receptacle possesses sufficient resiliency to permit the fin-bearing portion of the insert matrix to be pushed past the projection and into the fluid receptacle and to then remain confined by the projection within the fluid receptacle during inversion thereof.

8. The process of claim 7 wherein said projection is spaced from the mouth of the fluid receptacle by a distance sufficient to permit the fin-bearing portion of the insert matrix to remain stably poised adjacent the mouth of the fluid receptacle prior to being pushed past the projection and into the fluid receptacle.

9. The process of claim 8 wherein the distance by which said projection is spaced from the mouth of the fluid receptacle is substantially equal to or greater than the length of the fin-bearing portion of the insert matrix, whereby said fin-bearing portion will be substantially entirely enclosed by said vertical side walls while the insert matrix remains stably poised adjacent the mouth of the fluid receptacle prior to being pushed past the projection and into the fluid receptacle.

10. The process of claim 8 wherein said projection is spaced from the bottom of the fluid receptacle by a distance substantially greater than the length of the fin-bearing portion of the insert matrix, whereby the insert matrix may separate from the bottom of the fluid receptacle during inversion thereof to enhance the drainage of fluid therefrom.

11. The process of claim 10 wherein the fixed component is an antibody, the mobile component is an antigen at least a portion of which contains a radioactive label, and the reaction is the binding of the antigen to the antibody, and wherein step (d) comprises measuring the amount of radioactivity bound to the antibody immobilized on the reactive portion of the insert matrix in order to determine the amount of antigen bound, in order to determine the amount of antigen present in the fluid sample.

12. The process of claim 10 wherein the fixed component is an antibody, the mobile component is an antigen, and the reaction is the binding of the antigen to the antibody, and wherein step (d) comprises the steps of:
 (i) immersing the reactive portion of the insert matrix having antigen bound thereon in a second fluid containing a radioactively tagged antibody capable of binding with the bound antigen, and
 (ii) measuring the amount of radioactivity bound to the bound antigen in order to determine the amount tagged antibody which has bound to the bound antigen, in order to determine the amount of antigen bound, in order to determine the amount of antigen present in the fluid sample.

13. A test apparatus for carrying out a measurable reaction between a mobile component contained in a fluid sample and a fixed component immobilized on a solid phase matrix, comprising:
 (a) a fluid receptacle suitable for containing said fluid sample and for receiving a solid phase insert matrix by manual insertion thereof, said fluid receptacle having a retainer on the side wall of the inner surface thereof for confining at least the reactive portion of an insert matrix within the fluid receptacle during inversion thereof, said retainer comprising an integral convex projection on the inner surface of the receptacle corresponding to a concave indentation formed on the outer surface of the receptacle, and
 (b) an impermeable unitary insert matrix having a handle portion for enabling manual insertion of the insert matrix into said fluid receptacle and a reactive portion which is in contact with the fluid sample when inserted therein, said reactive portion having the fixed component immobilized thereon and having a generally open configuration which permits fluid to be poured into the fluid receptacle through said reactive portion and decanted from the fluid receptacle through said reactive portion by inversion of the fluid receptacle with the reactive portion of the insert matrix confined therein by said retainer.

14. A test apparatus as defined in claim 13, wherein the insert matrix includes a central rod, one end of said central rod forming the handle portion of the insert matrix, and wherein the reactive portion of said insert matrix comprises a plurality of elements attached at the other end of said central rod, and having essentially smooth plane or curved surfaces with the fixed component immobilized thereon, said elements being so arranged with respect to one another and the central rod and of a size and shape such that when the insert matrix is inserted into the fluid receptacle, the reactive portion of the insert matrix extends substantially throughout the depth of the fluid sample and the average diffusion distance of molecules of the mobile component to the surfaces of said elements is greatly reduced relative to the average diffusion distance of molecules of said mobile component to the fluid receptacle when no insert matrix is presented therein.

15. A test apparatus as defined in claim 14, wherein said elements comprise a plurality of fins extending outwardly from said central rod along a portion of the length thereof, and wherein said fluid receptacle includes substantially straight vertical side walls terminating in an open mouth at one end of said receptacle and a closed bottom at the opposite end of said receptacle.

16. A test apparatus as defined in claim 15, wherein said retainer comprises a convex projection on the inner vertical side wall surface of said receptacle corresponding to a concave indentation formed on the outer vertical side wall surface of said receptacle, said projection having dimensions sufficient to normally obstruct the insertion of the fin-bearing portion of the insert matrix into the fluid receptacle and its removal therefrom, and wherein at least one of said insert matrix and said fluid receptacle possesses sufficient resiliency to permit the fin-bearing portion of the insert matrix to be pushed past the projection and into the fluid receptacle and to then remain confined by the projection within the fluid receptacle during inversion thereof.

17. A test apparatus as defined in claim 16, wherein said projection is spaced from the mouth of the fluid receptacle by a distance sufficient to permit the fin-bearing portion of the insert matrix to remain stably poised adjacent the mouth of the fluid receptacle prior to being pushed past the projection and into the fluid receptacle.

18. A test apparatus as defined in claim 17, wherein the distance by which said projection is spaced from the mouth of the fluid receptacle is substantially equal to or greater than the length of the fin-bearing portion of the insert matrix, whereby said fin-bearing portion will be substantially entirely enclosed by said vertical side walls while the insert matrix remains stably poised adjacent the mouth of the fluid receptacle prior to being pushed past the projection and into the fluid receptacle.

19. A test apparatus as defined in claim 17, wherein said projection is spaced from the bottom of the fluid receptacle by a distance substantially greater than the length of the fin-bearing portion of the insert matrix, whereby the insert matrix may separate from the bottom of the fluid receptacle during inversion thereof to enhance the drainage of fluid therefrom.

* * * * *

UNITED STATES PATENT AND TRADEMARK OFFICE
CERTIFICATE OF CORRECTION

PATENT NO. : 4,425,320

DATED : Jan. 10, 1984

INVENTOR(S) : David A. Perry, Peter Stead

It is certified that error appears in the above-identified patent and that said Letters Patent is hereby corrected as shown below:

Column 4, line 25, after "as" the word "it" should be --is--.

Column 8, line 63, the number ''124" should be --24--.

Column 13, line 68, the number "16" should be --116--.

Column 14, 1. 20, within the parentheses, the word "normal" should be --nominal--.

Signed and Sealed this

Seventeenth Day of July 1984

[SEAL]

Attest:

GERALD J. MOSSINGHOFF

Attesting Officer

Commissioner of Patents and Trademarks